United States Patent [19]

Aubert et al.

[11] 4,299,858

[45] Nov. 10, 1981

[54] PROTEINS CONTAINING NUTRITIOUS MATERIALS AND FOOD COMPOSITIONS CONTAINING SUCH NUTRITIOUS MATERIALS

[75] Inventors: Jean P. Aubert; Francis Gasser, both of Paris; Robert Longin, Meudon La Foret, all of France

[73] Assignee: Institut Pasteur, Paris, France

[21] Appl. No.: 617,703

[22] Filed: Sep. 29, 1975

[30] Foreign Application Priority Data

Sep. 30, 1974 [FR] France .............................. 74 32889

[51] Int. Cl.$^3$ .............................................. A23K 1/00
[52] U.S. Cl. .................... 426/656; 426/623; 426/630; 426/807; 435/68; 435/253; 435/804; 260/112 R
[58] Field of Search ...................... 195/1, 96, 78, 100, 195/82, 97, 98; 260/112 R; 426/52–54, 656, 61, 623, 630, 636; 435/68, 253, 804

[56] References Cited

U.S. PATENT DOCUMENTS 3,821,080  6/1974  Kalina et al. ............... 260/112 R X

OTHER PUBLICATIONS

Stainer et al., "The Microbial World" Prentice Hall Publishers Inc. 1970 pp. 593–594 and 609–610.

Primary Examiner—R. B. Penland
Attorney, Agent, or Firm—Weiser, Stapler & Spivak

[57] ABSTRACT

The invention relates to nutritious materials containing proteins wherein said proteins are originated from osmosensitive microorganisms, i.e. microorganisms the cell walls of which are spontaneously broken when brought into contact with a medium of low osmotic pressure.

47 Claims, No Drawings

PROTEINS CONTAINING NUTRITIOUS MATERIALS AND FOOD COMPOSITIONS CONTAINING SUCH NUTRITIOUS MATERIALS

The invention relates to nutritious materials containing proteins, to food compositions containing such nutritious materials and to a process for their manufacture.

It is known that the world demand for proteins is in constant growth. The increase of this demand has further been stimulated in the past decades owing to the development of food compositions appropriate for promoting the rapid growth of domestic animals intended for the alimentation of man.

Proteins of vegetal origin, for instance, extracted from soya-bean are most often used for such food compositions. However, there are only few plants which are sufficiently rich in proteins having an amino acid composition which adequately meets the nutritional needs of animals and which, accordingly, can be used as such for the preparation of food compositions. As a result much research has been devoted to the discovery and use of microorganisms, yeasts or bacteria, which can be cultivated industrially, as a source of nutritious proteins.

The difficult accessibility of the proteins is a major difficulty encountered in the production of proteins obtained from yeasts or bacteria for the manufacture of food compositions. As a matter of fact these microorganisms comprise an external wall which is hardly hydrolysable. Particularly the digestive enzymes are totally inactive on these cell walls. The remarkable resistance of bacteria to the action of digestive enzymes is witnessed by the proliferation of a great number of bacterial species on the whole length of the digestive tract of superior animals, in an order of magnitude of $10^8$ to $10^{10}$ cells per gram of intestinal content, for instance in man or pig.

Many processes have been disclosed in which there is caused a rupture of the microorganism cell walls, such as by mechanical rupture, enzymatic lysis, etc. The difficulties encountered in carrying out these processes and their cost render them very uneconomical.

It has also been suggested to use dead cells whose walls are more or less degraded, as a source of proteins. The accessibility of the intracellular proteins is then improved, but is yet not satisfactory. However, even in this case, the remaining walls remain poorly digestible and also, owing to their presence in the food, alter the digestibility of the other cell components, particularly proteins.

The object of the invention is to obviate at least substantially these difficulties and more particularly to provide new protein-based nutritious material originating from microorganisms which is easily accessible and digestible.

The food material containing proteins according to the invention is characterized in that said proteins are essentially originated from "osmosensitive" microorganisms, particularly bacteria, the cell walls of which are spontaneously broken or ruptured, as soon as they are brought into contact with a medium of low osmotic pressure, such as soft water, that is water substantially free of salts, or water having a reduced content of metal salts, such as sodium chloride. Preferably recourse is made to those osmosensitive microorganism which are able to grow in a medium of high osmotic pressure, for instance sea water bacteria.

Advantageously recourse is had to osmosensitive microorganisms, the cell walls of which are caused to be ruptured when brought into contact with an aqueous saline solution containing less than 15 g/l of sodium chloride.

In accordance with one of the preferred embodiments of the invention the nutritious materials are formed of dried osmosensitive microorganisms, the cell walls of which have or have not been previously ruptured.

The invention also relates to food compositions which contain dried osmosensitive microorganisms or proteins extracted from these microorganisms, in association with other nutritious or digestible materials, notably such as those which are currently used (flours, carbohydrates, etc.) for the manufacture of food compositions, for instance for cattle, or more generally for livestock.

Several bacteria species having the above defined osmosensitive character as defined hereabove have already been disclosed. Among these species one finds the bacteria which are able to grow in marine media, particularly halophile bacteria. Osmosensitive bacteria are found in the groups of Pseudomonads, of Hyphomicrobium, of Spirochaetales, of Eubacterium, of Photobacterium, etc. Particular reference is made to groups of bacteria of such type, as defined in "Bergey's Manual of Determinative Bacteriology", 7th edition (1957) and 8th edition (1974), Williams and Wilkins Company, Baltimore. Reference is made particularly to the anaerobic or facultatively anerobic gram-negative bacteria, having osmosensitive properties, and notably to those which are disclosed in parts 7 and 8 of last mentioned edition of the Bergey's Manual.

Examples of suitable osmosensitive bacteria suitable for the preparation of food materials according to the invention are, for instance, Photobacterium species, for instance *Photobacterium leiognathi*, ATCC 25 521 and 25 587, respectively, or *Photobacterium phosphoreum*, ATCC 11 040.

The proteins contained in the liquid or aqueous Marine pseudomonad B 16 (ATCC 19 855), *Achromobacter fischerei; Achromobacter fischerei* strain Jamaica; *Vibrio costicolus; Halobacterium cutirubrum*, etc. . .

The strains can be isolated from natural media having a high osmotic pressure, notably from marine media, either directly, or from an enrichment culture, such as the interrupted enrichment culture according to the method of Whittenbury et al (*J. Gen. Microbiology* 1970, 61, 205). The selection of the most favorable species can be carried out by means of easy tests which consist in the determination of their aptitude to grow in a medium of high osmotic pressure, for instance in a solution of sodium chloride containing, for instance, more than 15 g/liter of sodium chloride, or of their sensitivity to osmotic shock, more particularly that caused by their being brought into contact with soft water, which causes the spontaneous rupture of the cell walls of the species under consideration. Preferably use is made of the species which possess high protein contents and, preferably, those in which the proportions of the amino acids which form said proteins are already balanced from the nutritive point of view. Particularly preferred osmosensitive bacteria are those which contain substantial proportions of lysine and of methionine. The strains to be used are normally selected among the non-pathogenic ones. Pathogenic strains may be used too, to the extent that they can be freed from their pathogenic character by conventional procedures.

Osmosensitive microorganisms, particularly osmosensitive bacteria, which are able to grow in a medium having a high osmotic pressure, can be obtained in large amounts by cultivation.

Advantageously, the above cultivation is carried out within sea water to which the essential nutriments necessary for the growth of the bacteria have been added, to the extent necessary (e.g. phosphates, nitrogen sources, carbon sources). Sea water is readily available, has a constant composition, is substantially free of contamination, notably of sporulated bacteria, and does normally not require sterilization. In those instances where sterilization would nevertheless appear to be desirable it would then only require a minimum consumption of energy.

According to a first alternative of the process of the invention for the production of food materials containing proteins originating from osmosensitive bacteria, the microorganisms, particularly the harvested bacteria, can be used as such, in the form of a humid paste, or preferably are dried and either stored as such, for their later incorporation into food compositions, or immediately incorporated into such compositions.

In those cases the rupture of the osmosensitive bacteria cell walls in such food compositions and, consequently, the access to their protein contents, occur spontaneously, when contacted with the gastric juice, in the stomach of the host which absorbs them.

The cell walls may also be pre-ruptured, for instance by contacting the bacteria with amounts of a liquid having low osmotic pressure, such as soft water, sufficient to cause said rupture, whereby the food material is then formed of osmosensitive bacteria, the cell walls of which are preferably dried.

In a general manner, the osmosensitive bacteria (whether their walls have been pre-ruptured or not) can be used under all forms suitable for the alimentation of living beings, particularly animals (dry powders, humid pastes, suspension of ruptured bacteria in a medium having low osmotic pressure, notably soft water) or for human alimentation, the above composition then preferably also containing flavoring components.

The presence of the walls (whether ruptured previously or not) in the food compositions obtained does not represent a serious drawback, particularly does not substantially alter the digestion. As a matter of fact, the walls of osmosensitive bacteria are generally extremely thin, so that their relative proportion in weight with respect to their protein contents is low.

In that respect, recourse is advantageously had to osmosensitive bacteria in which the proportion in weight of the walls with respect to the whole bacteria is less than about 5%, preferably of the order of 2% or less.

The problem of the digestibility of the walls can also be completely obviated when recourse is had to the second process alternative according to the invention which comprises bringing the harvested osmosensitive bacteria in contact with a sufficient quantity of a hypotonic medium, such as soft water, for causing the rupture of the walls of most of the bacteria and for further enabling a maximum amount of the protein which they contain to dissolve in the medium, then removing the insoluble fraction and recovering the liquid phase containing the proteins in a dissolved state. The above bringing into contact may be performed easily by simply suspending the bacteria in the aqueous medium.

The proteins contained in the liquid or aqueous fraction can be recovered in the dried state by evaporating the water under conditions compatible with the preservation of the proteins, particularly of their nutritive value, according to any of the current well known methods in the protein art. The products can also be lyophilised, although this method would be rather uneconomical when applied to large amounts of food material. Any other drying process can of course be resorted to.

The dry product obtained which contains the dry proteins, can then be incorporated as such, if need be after a preliminary crushing treatment, into food compositions.

Other features of the invention will appear in the course of the following disclosure of a non-limitative production example of a food material or principle containing proteins from a typical culture of osmosensitive bacteria.

The species used, *Photobacterium leiognathi*, has been described by Boisvert, Chatelain and Bassot in the "*Annales de l'Institut Pasteur*" (1967) 112, 520–524. Strains of these bacteria are deposited in the American Type Culture Collection under the numbers 25521 and 25587 respectively. These strains have no pathogenic power. They can be cultivated within a medium containing from 15 to 40 g of sodium chloride per liter.

The media which can be used for the precultivation and the cultivation (upkeeping of the culture) can be as follows:

Medium of precultivation—NaCl, 30 g; $PO_4HNa_2$, 12 $H_2O$.18.7 g; $PO_4H_2K$, 2 g; $SO_4Mg$. 7 $H_2O$, 0.2 g; $SO_4Fe$, 0.05 g; $ClNH_4$, 2 g; distilled water for completing to 1 liter. Before use the pH is first adjusted at 7.2 and the medium is sterilised during 30 minutes at 115° C. Just before seeding, a solution of sterile glucose is added to obtain a final concentration of 3 g of glucose per liter.

Cultivation Medium (upkeeping of the culture)—NaCl, 30 g; $PO_4H\ Na_2.12H_2O$, 18.7 g; $PO_4H_2K$, 2 g; $PO_4N(NH_4)_2$, 0.5 g; $SO_4Mg.7\ H_2O$, 0.2 g; $SO_4Fe$, 0.05 g; bacteriological peptone, 5 g; yeasts, 5 g; glucose, 3 g; distilled water up to 1 liter. Before use the pH is adjusted at 7.2 and the medium is treated in the autoclave at 115° C. for 30 minutes.

An industrial culture can be carried out within sea water, which has been first filtered and which contains the following ingredients:

Phosphoric acid up to a final concentration of 0.1 g/l (pH adjusted at 7.2 with sodium hydroxide after addition of the acid), Amonium chloride, 2 g per liter, Glucose, 3 g per liter, $FeSO_4.7\ H_2O$, 50 mg per liter.

This medium need not be sterilised.

The culture is carried out in a fermenter at 30° C. under agitation and forced aeration. The medium is then sowed with about $1.10^8$ bacteria per milliliter. The pH is kept constant. The growth rate obtained is of 0.6 divisions/hour.

At the end of the exponential growth phase the bacteria can be harvested by centrifugation (or by any other means). The yield in bacteria is greater than 1 g weight of dry bacteria per liter of medium (after deduction of the dry weight of the mineral salts in the medium). The bacteria yield can be improved by increase of the concentrations of the different components in the medium.

Owing to their osmotic fragility the harvested bacteria can be used as protein source either directly after drying of the harvested bacterial paste, or after a lysis operation with, for instance, 4 volumes of water per volume of humid bacterial paste (or of 1 liter of water per 70 g of dry paste. This simple osmotic shock is sufficient for lysing the bacteria whereby their protein content is freed. The dissolved proteins can be recovered by evaporation at a temperature below 100° C., under reduced pressure.

The food material so obtained has the following composition:

| Composition of the nutritive material | % of dry bacterial weight |
|---|---|
| Proteins | 55 |
| Lipids | 28.6 |
| Ribonucleic acids | 10 |
| Desoxyribonucleic acids | 1.1 |
| Walls | 1.9 |

| Aminoacid compositions of the protein fraction of the nutritious material or principle | | | |
|---|---|---|---|
| | % in weight | | % in weight |
| Glycine | 4.44 | Lysine | 8.9 |
| Alanine | 5.6 | Arginine | 6.2 |
| Valine | 6.9 | Aspartic acid | 11.8 |
| Leucine | 8.2 | Glutamic acid | |
| Isoleucine | 5.6 | | 17.4 |
| Serine | 3.24 | Phenylalanine | 5.3 |
| Threonine | 4.4 | Tyrosine | 3.3 |
| Histidine | 2.0 | Tryptophane | 1.4 |
| | | Methionine | 2.0 |
| | | Proline | 3.1 |

As can be seen from these results, the proteins so obtained are well balanced from a nutritive point of view.

The above results also show that the weight proportion of the walls can be held as negligible, so that the nutritious materials thus obtained which contain proteins can be used as such in food compositions without a previous lysis of the bacteria or separation of the walls, under conditions substantially as disclosed hereinbefore.

Thus, the invention provides a new source of nutritious proteins and new nutritious materials which can be obtained very easily, which can be pretreated without difficulties if desired (rupturing and if need be removal of the cell walls), and which is highly digestible by the host, whether the walls have been first separated or not).

We claim:

1. A process for obtaining an animal food material which comprises exposing the cells of a culture of osmosensitive microorganisms to a medium of low osmotic pressure to cause the rupture of the cell walls of said osmosensitive microorganisms.

2. A process for obtaining an animal food composition of high nutritive value having a high protein, including amino acid content which comprises:
lowering the osmotic pressure of a harvested culture of protein-containing osmosensitive microorganisms to a pressure sufficiently low to rupture the cell walls of the microorganisms, said microorganisms having cell walls which are essentially not hydrolyzable by digestive enzymes and which cell walls are so fragile that they rupture spontaneously upon contact with a medium of osmotic pressure less than 15 g/l of salt content and which is lower than that in which the microorganism is capable of growing, and
collecting a humid paste of the animal food composition comprising the non-viable microorganisms and cellular material.

3. The process of claim 2 which comprises drying the humid paste of the animal food composition so collected.

4. The process of claim 2 which comprises separating the ruptured cell walls.

5. The process of claim 2 which comprises drying the collected paste composition comprising cell walls and released proteins for use as the food composition.

6. The process of claim 5 which comprises processing the humid paste into a food composition suitable for feeding livestock.

7. The process of claim 2 which further comprises the step of drying the paste.

8. The process of claim 2 wherein the lowering of the osmotic pressure is carried out under alkaline conditions.

9. The process of claim 2 which comprises concentrating the collected animal food composition material.

10. The process of claim 2 which comprises incorporating the humid paste collected into a food composition suitable for feeding livestock.

11. The process of claim 10 which further comprises drying the food composition.

12. A process for obtaining an animal food material of high nutritive value having a high protein, including amino acid content, which comprises:
subjecting cells of a culture of protein-containing osmosensitive microorganisms to an osmotic pressure sufficiently low to rupture the cell walls of the microorganisms, said microorganisms having cell walls which are essentially not hydrolyzable by digestive enzymes and which cell walls are so fragile that they rupture spontaneously upon contact with a medium of osmotic pressure less than 15 g/l of salt content and which is lower than that in which the microorganism is capable of growing, thereby releasing proteins contained in the microorganisms,
dissolving the proteins in an aqueous medium,
removing an insoluble cell fraction, and
collecting a liquid phase of said aqueous medium containing the dissolved proteins.

13. The process of claim 12 which comprises the step of drying the liquid phase containing the collected proteins.

14. The process of claim 12 where the step of removing the insoluble cell fraction is omitted and the cell fraction is collected with the proteins and dried.

15. A food material comprising a medium free, harvest of digestible protein-containing osmosensitive, non-viable microorganisms, the cell walls of which are fragile enough to spontaneously rupture upon contact with gastric juice in the stomach of a host to make available digestible protein.

16. The food material of claim 15 wherein the osmosensitive microorganisms are bacteria.

17. The food material of claim 15 which is whole osmosensitive microorganisms.

18. The food material of claim 15 which is dry whole cells.

19. The food material of claim 15 wherein the proportion in weight of the cell walls with respect to the whole cells is less than 5%.

20. The food material of claim 19 wherein this weight proportion is approximately 2%.

21. The microorganism of claim 15 which is capable of growth in a medium of high osmotic pressure.

22. The food material of claim 15 wherein the cell wall is capable of rupture upon exposure to an aqueous saline solution of less than 15 g/l of NaCl.

23. The food material of claim 15 wherein the microorganism is taken from the group of Photobacteria, Achromobacter, *Vibrio costicolus*, and halobacteria.

24. The food material of claim 15 wherein the microorganisms are halophile bacteria.

25. The food material of claim 24 wherein the halophile bacteria are selected from the group of Pseudomonas, Hyphomicrobium, Spirochaetales, Eubacterium and Photobacterium.

26. The food material of claim 15 wherein the microorganisms are marine bacteria.

27. The food material of claim 15 which is dry.

28. The food material of claim 15 which is a paste.

29. The food material of claim 15 which is an aqueous solution.

30. The food material of claim 15 which is an aqueous suspension.

31. The food material of claim 15 wherein the cell walls are ruptured.

32. The food material of claim 15 which is free of cell walls.

33. The digestible protein of claim 15 which includes lysine and methionine.

34. The food material of claim 15 which comprises cell walls and digestible proteins.

35. The food material of claim 34 which comprises the digestible proteins and other nutritious or digestible materials.

36. The food material of claim 15 which is a protein extract of the harvest.

37. The food material of claim 36 which is dry.

38. The food material of claim 36 which is an aqueous paste.

39. A composition of human manufacture comprising animal food of high nutritive value, high protein and amino acid content, said composition comprising a nutrient material and a biologically pure humid paste of concentrated, protein-rich, living osmosensitive bacteria microorganisms grown in a controlled environment and collected therefrom by man, said bacteria having cell walls which are essentially non-hydrolyzable by digestive enzymes, but which are so fragile that they spontaneously rupture upon contact with the gastric juice of an animal host thereby releasing their digestible protein for alimentation wherein the nutrient material and biologically pure humid paste are present in an amount sufficient to provide a suitable animal food ration.

40. The food composition of claim 39 which is free of the cell walls.

41. The food composition of claim 39 which is a protein extract.

42. The food composition of claim 41 which is an aqueous solution.

43. The food composition of claim 41 which is an aqueous suspension.

44. The dried composition of claim 39.

45. The composition of claim 39 wherein the cell walls of the bacteria are so fragile that they spontaneously rupture upon contact with a medium having osmotic pressure less than 15 g/l of salt content, said osmotic pressure being lower than that in which the bacteria is capable of growing thereby making the digestible protein content of the bacteria available to an animal host when the food is consumed.

46. The composition of claim 45 wherein the cell walls are ruptured.

47. The composition of claim 45 wherein the composition is cell wall-free.

* * * * *